(12) United States Patent
Jodaikin et al.

(10) Patent No.: US 7,850,453 B2
(45) Date of Patent: Dec. 14, 2010

(54) RESHAPABLE DEVICE FOR FIXATION AT A DENTAL SITE

(75) Inventors: Ahron Jodaikin, Kiryat Telstone (IL); Hilary Jodaikin, Kiryat Telstone (IL)

(73) Assignee: Coll Partners Ltd., Road Town, Tortola (VG)

( * ) Notice: Subject to any disclaimer, the term of this patent is extended or adjusted under 35 U.S.C. 154(b) by 138 days.

(21) Appl. No.: 11/890,986

(22) Filed: Aug. 8, 2007

(65) Prior Publication Data

US 2009/0042161 A1 Feb. 12, 2009

(51) Int. Cl.
*A61C 5/00* (2006.01)

(52) U.S. Cl. .......................................... 433/215; 433/80

(58) Field of Classification Search .................. 433/25, 433/18, 80, 215; 424/435, 469
See application file for complete search history.

(56) References Cited

U.S. PATENT DOCUMENTS

| | | | |
|---|---|---|---|
| 3,679,360 A | 7/1972 | Bernard et al. |
| 4,556,561 A | 12/1985 | Brown et al. |
| 4,576,190 A | 3/1986 | Youssef et al. |
| 4,638,823 A | 1/1987 | Newman et al. |
| 4,837,007 A | 6/1989 | Duckworth et al. |
| 4,923,683 A | 5/1990 | Sakuma et al. |
| 4,938,763 A | 7/1990 | Dunn et al. |
| 5,077,049 A | 12/1991 | Dunn et al. |
| 5,278,201 A | 1/1994 | Dunn et al. |
| 5,324,519 A | 6/1994 | Dunn et al. |
| 5,373,599 A | 12/1994 | Lemon et al. |
| 5,460,803 A | 10/1995 | Tung et al. |
| 5,579,786 A | 12/1996 | Wolk et al. |
| 5,605,677 A | 2/1997 | Schumann et al. |
| 5,639,840 A | 6/1997 | Fife et al. |
| 5,733,950 A | 3/1998 | Dunn et al. |
| 5,739,176 A | 4/1998 | Dunn et al. |

(Continued)

FOREIGN PATENT DOCUMENTS

DE 202006003819 U1 6/2006

(Continued)

OTHER PUBLICATIONS

Miller, M and Truthe, T. Jada 124:32 (1993).

(Continued)

*Primary Examiner*—Ralph A Lewis
*Assistant Examiner*—Eric Rosen
(74) *Attorney, Agent, or Firm*—Roach Brown McCarthy & Gruber, P.C.; Kevin D. McCarthy

(57) ABSTRACT

Disclosed is a reshapable retention device for insertion at a dental site and contact with adjacent dental surfaces, for the controlled delivery to the dental site of at least one material having a predetermined intraoral activity, with at least one matrix containing the material. The device is adapted for physically affixing at the dental site. The device has a first configuration in which the overall dimensions of the retention device are larger than at least one dimension of the dental site, which is reshapable to a second in which at least one dimension of the retention device is reduced. In the second configuration the retention device has a predetermined shape having contours for affixing at the dental surfaces. The device is affixed to the dental site in its second configuration.

51 Claims, 7 Drawing Sheets

U.S. PATENT DOCUMENTS

| | | | |
|---|---|---|---|
| 5,875,799 | A | 3/1999 | Petrus |
| 6,106,811 | A | 8/2000 | Gibbs |
| 6,287,120 | B1 | 9/2001 | Wiesel |
| 6,343,932 | B1 | 2/2002 | Wiesel |
| 6,521,215 | B2 | 2/2003 | Okay |
| 6,565,960 | B2 | 5/2003 | Koob et al. |
| 7,118,376 | B2 | 10/2006 | Jodaikin et al. |
| 2003/0068284 | A1* | 4/2003 | Sagel et al. .................. 424/53 |
| 2005/0175959 | A1* | 8/2005 | Jodaikin et al. ............... 433/80 |

FOREIGN PATENT DOCUMENTS

WO      WO 98/16503      5/1998

OTHER PUBLICATIONS

PCT International Search Report for corresponding PCT application.
Bailey, A.J. et al., Biochem. Biophys. Res. Commun. 35:663-671 (1969).
Orban J.M. et al. J of Biomedical Materials Research 68A:756-762, (2004).
Bourges et al Adv. In Colloid and Interface Sci 215-228: 2002.
Bourges X. et al. Biopolymers 63:232-238: 2002. . . .
Jodaikin, A. and Goldstein, S., J. Dent. 16:140-144, (1988).
Harris, N.O. and Christen, A.G. Primary Preventive Dentistry 4th Ed Norwalk Appleton Longe 1995.
Wu. H. et al ,abstract from Hua Zi Kou Qiang Yi Xue Za Zhi 18: 219-221, (2000).
Zimmerman, B.F. et al J. Dent. Res. 63:689-692 (1984).
Fuji 1X GP® fast by GC Inc. . . .
Hormann, H. In Sigel, H. Metal Ions in Biological Systems vol. 3 New York Marcel and Dekker p. 105, 1974.
Mjor, I.A. Quintessence Int.29: 600- 602, 1998.
Remington's Pharmaceutical Sciences, Gennaro A. R. ed., Mack Publishing Company, Easton, Pennsylvania, 1990.
Inaba D. et al., Caries. Res. 30:218-224 (1996). . . .
Gilmore HW et al, Operative Dentistry, 3rd Ed., CV Mosby Company, p. 25-26.
US Design U.S. Appl. No. 29/234,883. . . .
Jenkins, G.N. The Physiology and Biochemistry of the Mouth p. 495, 1978, Blackwell Scientific Publishing.
Craig, R.G. et al Dental Materials, Properties and Manipulation p. 2-28, 2nd Ed 1979 CV Mosby Co.
Koulourides, T., Art and Science of Dental Caries Research pp. 355-378, 1968.
Poole, D.F,G. And Silverstone, L.M., Hard tissue Growth Repair and Remineralisation, pp. 35-52, Ciba Fondation Symposium No. 11, Elsevier Scientific Publishing Company, 1973.
Pearce E.I.F and Moore, A.J., J. Dent Res 64;416-421, 1985.
A guide to the use of fluorides JADA 113:504-564, 1986, prepared by the National Fluoride Task force of the NFDH.
Levi-Kalisman, Y. et al J. Chem Soc. Dalton Trans 2000: 3977-3982, 2000.
Wefel, J.S. and Harless, J.D. J. Dent Res 66: 1640-1643, 1987.
Takagi, S. et al Caries Res 34: 281-288 (2000). . . .
Addadi, L. and Weiner, S. Angew, Chem. Int. Ed. Engl. 31:15, 3-169, (1992).
Kodaka, T. et al Caries Res 26 : 69-76 (1992).
Addadi, L. et al ACS Sym. Series No. 444, 1991.
Turezyn, R. et al J. Biomater Sci. Polym Ed 11:217, (2000).
Wefel J.S. et al. Am J. Dent. 8, 217-220 (1995). . . .
Caufield, P.W. And Navia, J.M. in the Biological Basis of dental caries, Menaker, L. 406-407, Harper and Row, (1980).
Clarkson B.H. et al. J. Dent. Res. 60:1912-1920 (1981).
Shellis, R.P. et al Eur. J. Oral Sci 110: 392-395, (2002).
Clarkson, B.H. et al Caries Res 32: 357, 1998. . . .
Tanaka, K. and Iijima, Y. J. of Dent. 29: 421-426 (2001).
Dental Therapeutics Digest Odontos Pub Inc.: Kay L.W. Drugs in Dentistry, Bristol 1972.
O'Brien, W.J. and Ryge, G. An Outline of Dental Materials, Saunders 1978.
Steinberg, D et al., J. Dent. Res. 67-208 Abstract No. 767, 1988.
Kopel, H.M. et al., J. of Dent. for Child 47: 425-430, (1980)) and Periochip®.
Vandelli, M.A. et al J. of Controlled Release 96,67-84 (2004).
Traub W., and Piez, K., A. Adv. Protein Chem. 25:243-352, 1971.
Davis, B.A. et al Caries Res 35, 331-337, (2001). . . .
Takatsuka, T. J. Dent Res. Sp Iss. A #2815 (2002). . . .
Loty C et al J. Biomed. Mat. Res. 49, 423 abstract (2000). . . .
Cury, J.A. et al Caries Res. 37, p. 194-199 (2003). . . .
Exterkate, R.A.M. et al J. Dent Res. 72 1599-1603 (1993).
Zhang et al J. Clin. Dent 14: 23-28 (2003). . . .
Addadi, L. et al ACS Sym. Series No. 444, p. 13-27 (1991). . . .
Addadi et al in Chemistry and Biology of Mineralized Tissues, Ed. Slavkin, H. and Price, P. Elsevier Sci. Pub. BV 153-162 (1992).
Addadi, L. and Weiner, s. Angen. Chem. Int. Ed. Engl. 31: 153-169 (1992).
Jodaikin, A. and Goldstein, S. J. Dent 16-140-144, (1988).
Paine, M.L. et al JADA 129, 69-77, (1998). . . .
Zhang, Y.P. et al J. Clin. Dent 14: 23-28, (2003). . . .
Glickman I., Clinical Periodoutology, fourth edition, Saunders p. 18-19 (1972).
Kay L.W. Drugs in Dentistry, Bristol p. 242-243, 254-255 (1972). Periochip®. . . .

* cited by examiner

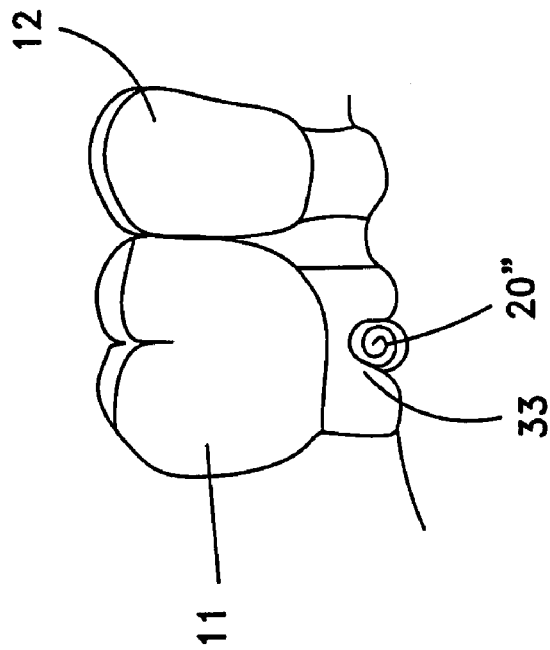
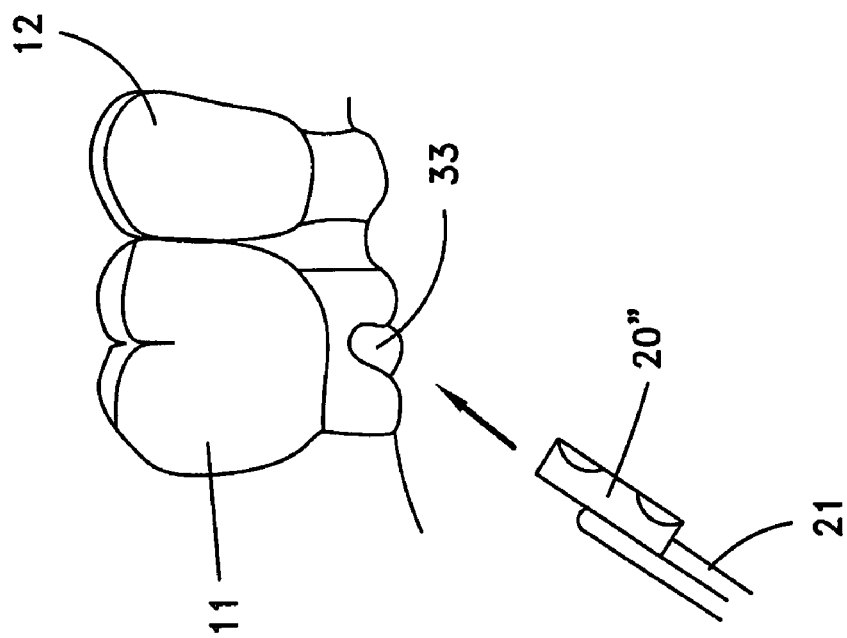
Fig. 3b
Fig. 3a

Section xx-xx

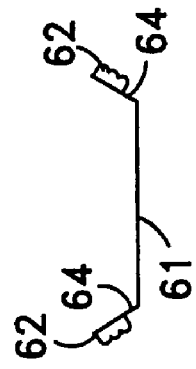
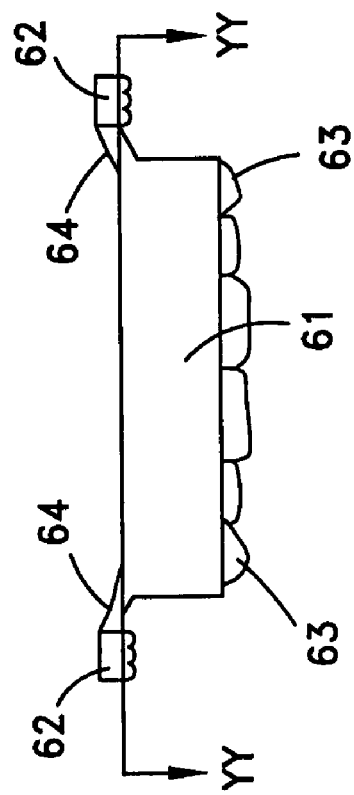
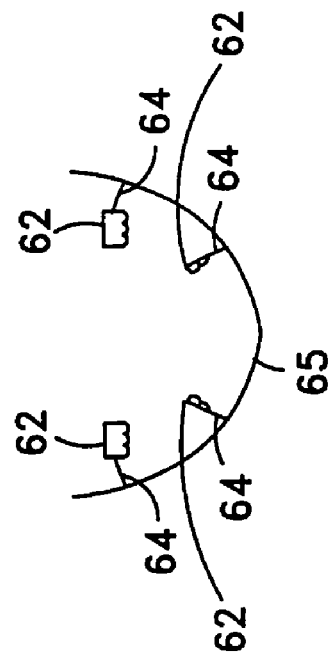

RESHAPABLE DEVICE FOR FIXATION AT A DENTAL SITE

FIELD OF THE INVENTION

The present invention relates generally to oral devices. In particular, the present invention relates to oral devices for retention at dental sites within the intraoral cavity to enable, inter alia, any one of the prevention, treatment, diagnosis, elimination, and retardation of oral and other diseases or problems. More particularly, the present invention relates to the chemical treatment of dental surfaces, or for chemical and/or physical restoration of teeth. Even more particularly the present invention is directed at the delivery of fluoridizing and other agents to or from interproximal sites among others.

BACKGROUND OF THE INVENTION

A significant percentage of dental caries (demineralization, decay) occurs between teeth (interproximally, aproximally). This difficult, inaccessible region has been recognized as a problem for more than half a century. Approaches have ranged from grinding of the interproximal surfaces to make them self-cleansing and thus caries "immune" (Mjor, I. A. Quintessence Int. 29: 600-602, 1998) to flossing between the teeth which requires fastidious patient compliance and smooth surfaces. The inclusion of fluoride (U.S. Pat. No. 4,638,823) and other agents in dental floss (U.S. Pat. No. 5,875,799) and other electric (U.S. Pat. No. 5,579,786) or mechanical and chemical devices (U.S. Pat. Nos. 4,576,190, 4,638,823 and 5,373,599) does not appear to have significantly reduced interproximal caries. There is thus, a need to develop a technique or device which overcomes these limitations and the disadvantages of flossing between the teeth.

Various means of chemically preventing or treating such lesions, as well as other problems such as discoloration and sensitivity are described by the inventors of the present invention in U.S. Pat. No. 7,118,376 and its co-pending U.S. Continuation In Part Application, Publication No. 2005-0175959, the contents of which, including publications referenced therein, is fully incorporated herein by reference.

In U.S. Pat. No. 7,118,376 the inventors of the present invention, describe a system for the controlled delivery of at least one material having a predetermined intraoral activity to an interproximal site of at least one dental surface in an oral cavity. The system comprises a polymeric matrix containing the said material. The system is sufficiently flexible for insertion at the interproximal site to be physically affixed thereat and sufficiently tough to maintain mechanical integrity at the interproximal site for the required amount of time and for a predetermined amount of time. The interproximal site is defined in U.S. Pat. No. 7,118,376 as an area of contact and surrounding surfaces between the dental surface and an adjacent dental surface. The co-pending U.S. Continuation In Part Application, Publication No. 2005-0175959, discloses the delivery of a predetermined portion of the at least one matrix to the interproximal site in a controlled single, bi or multiphase pattern.

However, the system described in U.S. Pat. No. 7,118,376 and its co-pending U.S. Continuation In Part Application, Publication No. 2005-0175959 is not directed to gingival and periodontal disease, or to the general systemic treatment or prevention related to the oral cavity and digestive system. Moreover, they do not relate to subtle anatomic nuances of the dentition and gingival and periodontal tissue in healthy or pathologic states.

The restoration of interproximal cavities, for example dental filling procedures, requires packed filling material to be retained in position in a tooth for a period of time. A thin flexible strip made of metal, plastic or other suitable material, known as a dental matrix band (or band, or matrix) is typically wrapped around the sides of the tooth being restored to maintain the filling in place while and after the filing has been placed to prevent the filling from distorting or flowing out of the desired tooth contour. Thus, a matrix band acts as a template to facilitate reestablishment of lost tooth contour by the filling material. A small wedge is often used, lodged in the interproximal space between the band and adjacent tooth to urge the band into close contact with the tooth being restored, and thus ensure that the band is held properly in place. A retention device that is fine tuned to anatomical nuances of the interproximal site and that limits and avoids the need for a wedge will facilitate proper placement of the matrix band at the interproximal site without encroaching on and/or causing damage to the gingiva or at least limiting such damage. Moreover, a retention device that itself acts as a template to facilitate reestablishment of lost tooth contour by the filling material may minimize costs involved with such procedures by reducing the amount of time and maximizing efficiency of the procedure.

It is therefore an object of the present invention to provide a retention device for physically affixing at a dental site.

An additional object of the present invention is to provide a reshapable device for physically affixing at a dental site to have a desired or predetermined activity to at least one desired dental surface in the oral cavity, or into the oral cavity, which overcomes the disadvantages of the prior art.

It is another object of the present invention to provide such a device that is particularly directed to the anatomical areas of interproximal sites and furcations.

It is yet another object of the present invention to provide a system for fixing a plurality of devices intraorally.

It is a further object of the present invention to provide such a device that is configured according to the contours of dental and soft tissue surfaces.

It is still another object of the present invention to provide such a devoice that employs at least one matrix as a carrier for active material.

It is an additional object of the present invention to provide such a device in which the matrix for the active material may be biodegradable, resorbable or non-resorbable.

It is another object of the present invention to provide such a device which is particularly adapted for physical fixation at a dental site, for at least a predetermined time period, typically sufficient to enable the controlled or sustained delivery of a required quantity of the active material from the matrix or matrices to the surfaces and/or oral cavity.

It is another object of the present invention to provide such a device in which the physical affixing of the device is by way of a physical property of the matrix, in particular wherein the matrix comprises a hydrophilic polymer which softens and swells in situ by the hydration thereof in the oral cavity after accommodation at the dental site.

It is another object of the present invention to provide such a device which is adapted on the one hand to accommodate the matrix and align the same with the dental site, and on the other hand is also adapted for affixing at the site by virtue of its shape, configuration and elasticity/resilience of the material from which it is made. In particular, such adaption includes sufficient elasticity and toughness of the matrix material, which are important criteria when positioning the matrix between teeth.

It is another object to provide such a system wherein the device is sufficiently flexible for insertion into an interproximal site, and at the same time of sufficient toughness to maintain mechanical integrity thereat, while being soft enough not to be a source of discomfort within the oral cavity prior to its removal or biodegration.

It is another object of the present invention to provide any one or combination of a plurality of chemical and other agents that have a desired activity at the dental site, in particular such as to enable inter alia the cleaning, prevention, treatment, diagnosis, cosmetic treatment (whitening/bleaching and mouth/breath freshening), elimination or retardation of dental caries at tooth surfaces or at tooth interfaces with restorations or prostheses or to treat gingival or periodontal disease.

It is another object of the present invention to provide a system that is shaped to fit over a portion of, or an entire single dental arch.

It is another object of the present invention to provided such a device that is designed to release a chemical agent into the saliva for a desired or predetermined activity therewithin or in the digestive tract or absorbtion into the body.

It is another object of the present invention to provide such a device which includes at least one adhering agent.

It is another object of the present invention to provide such a device in a specific, controlled micro-environment which selectively excludes at least one element or molecule present in the mouth by way of a physical or chemical property of the matrix or matrices.

It is another object of the present invention to provide such a device in a specific, controlled micro-environment which optimizes the delivery of a least one element, molecule or agent to the said dental site. The said element, molecule or agent can be exogenous, from the device, or endogenous, e.g. directly or inderectly from the saliva.

It is another object of the present invention to provide such a system that employs at least one matrix to deliver a single phase controlled release pattern or a bi- or multiphase controlled release pattern to deliver at least one agent at an appropriate or optimal time, stage, manner or form.

It is another object of the present invention to provide such a system that employs at least one bi- or multi-layer or bi- or multi-located matrix to provide a single phase, biphase or multiphase controlled release system.

It is another object of the present invention to provide such a system that employs at least one matrix which keeps the active material or materials inactive by chemical means such as inhibition or physical separation in order to allow at least one agent to be delivered at an appropriate or optimal time, stage, manner or form.

It is another object of the present invention that the device is adapted to facilitate affixing at least one matrix band at the interproximal site to restore at least one cavity.

It is another object of the present invention that the device itself is adapted physically or chemically to allow the restoration of at least one interproximal cavity.

Additional objects and advantages of the present invention will become apparent as the description proceeds.

SUMMARY OF THE INVENTION

Thus, the present invention provides a method for the prevention and/or treatment of dental caries in a patient in need thereof, comprising applying at a dental site of said patient the matrix or matrices according to the invention, wherein the material is a fluoridation agent. Said material is selected from the group consisting of sodium fluoride, stannous fluoride, acidulated phosphate fluoride, calcium fluoride, an amine fluoride, fluoroaluminosilicate glass and any mixture thereof.

Alternatively, the material of the present invention is an amorphous mineral. Said material is selected from the group consisting of amorphous calcium phosphate, amorphous calcium phosphate fluoride, amorphous calcium carbonate phosphate, amorphous calcium carbonate phosphate fluoride, amorphous calcium fluoride and dicalcium phosphate dehydrate.

Alternatively, the material of the present invention is a crystalline mineral. Said material is selected from the group consisting of aragonite, brushite, calcite, dahltite, ferrhydrite, fluoroapatite, hydroxyapatite, lepidocrocite, magnetite, octocalsium phosphate, vaterite and whitlockite.

Alternatively, the material of the present invention is made of an organic material. Said material is selected from the group consisting of macromolecules such as acidic proteins, glycoproteins or sulfated polysaccharides, or smaller molecules such as polyaspartic or polyglutamic acid.

Alternatively, the material of the present invention is an enhancing agent or further active agent. Said material is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium malate, calcium maleate, calcium propionate, calcium vaerate, alkali salts, ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate.

Alternatively, the material of the present invention is an acidifying, buffering or pH regulating agent. Said material is selected from the group consisting of acidulated phosphate fluoride, citric acid, sodium citrate, sodium bicarbonate, calcium carbonate, arginine and polyacrylic acid fully neutralized with alkalimetal ammonium or (alkylol) amine compound sodium polyacrylate.

Alternatively, the material of the present invention is an antimicrobial agent. Said material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds.

Alternatively, the material of the present invention serves as a cleaning agent. Said material is selected from the group consisting of sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium laureth carboxylate, sodium dodecyl benzenesulfonate, poloxamers, polyoxyethylene sorbitan esters, fatty alcohol ethoxylates, polyethylene oxide, cocamidoppropyl betaine, sodium bicarbonate, monosodiumphosphate, sodium hydroxide, potassium hydroxide, sodium carbonate and imidazole.

Alternatively, the material of the present invention serves as an effervescing agent. Said material uses a sodium bicarbonate/citric acid system.

Alternatively, the material of the present invention serves as a tooth desensitizing agent. Said material is selected from the group consisting of fluorides, potassium citrate, potassium chloride, potassium tartrate, potassium bicarbonate, potassium oxalate and potassium nitrate.

Alternatively, the material of the present invention serves as a tooth whitening or bleaching agent. Said material is selected from the group consisting of hydrogen peroxide, carbamide peroxide metal chlorites, perborates, percarbonates, peroxyacids, persulfates, urea peroxide, calcium peroxide, calcium chlorite, barium chlorite, magnesium chlorite, lithium chlorite, sodium chlorite, potassium chlorite, hypochlorite, chlorine dioxide, sodium percarbonate, oxones, and protease.

BRIEF DESCRIPTION OF THE FIGURES

In the drawings:

FIG. 3(a) illustrates a side elevation view of a bucal portion of two lower posterior teeth similar to that shown in FIG. 1(a) and FIG. 2(e), showing periodontal disease resulting in gingival and bone recession, and showing a rolled retention device being inserted with tweezers into a furcation of a molar tooth.

FIG. 3(b) illustrates the rolled retention device in situ, positioned in the furcation.

FIG. 6(a) illustrates a frontal (facial) device view of a strip with two distal retention devices as shown in FIG. 4(c) in order to retain the said strip between the first bicuspids (premolars) and canines by means of the retention devices which are attached to the strip by means of an extension arm.

FIG. 6(b) illustrates a top view of the embodiment of FIG. 6(a) taken along line YY-YY thereof.

FIG. 6(c) illustrates a top view of a longer strip that covers the facial side of an entire dental arch with four retention systems.

DETAILED DESCRIPTION OF THE PREFERRED EMBODIMENTS

Figure 1A:
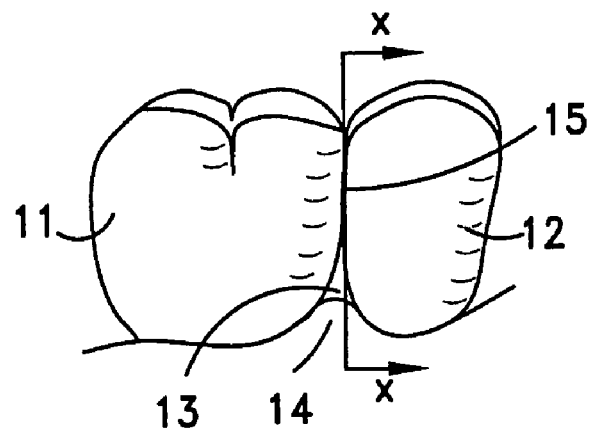
FIG. 1(a) illustrates a side, elevation view of a lingual portion of two lower posterior teeth (a molar and bicuspid (premolar)), showing the space between these two teeth (the interproximal or aproximal space), the gingival papilla and the contact area.

The present invention is defined by the claims, the contents of which are to be read as included within the disclosure of the specification, and will now be described by way of example with reference to the accompanying Figures.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The present invention relates to a device for the controlled or sustained delivery of a material or materials having a predetermined intra-oral activity to dental surfaces of the oral cavity, typically tooth surfaces or carious lesions, and in particular to interproximal sites or furcations, the device comprising a matrix or matrices containing said material or materials. The matrix or matrices is adapted for the controlled or sustained release of the active material or materials, and is further adapted for physically affixing at the dental site, for at least a predetermined time period that is correlated to the delivery of a predetermined portion of said material or materials to said site. This time period typically depends on the nature of the active material or materials and on the subject being treated, and may comprise a few seconds while a chemical activator, an electrical current, or a heat or light source such as a laser is administered to about four to eight hours during interproximal caries prevention or treatment. It is to be appreciated that a major factor in establishing the rate of release of the active material or materials is the structure of the polymeric matrix or matrices as a single uniform unit, multi-layer or a multi-location form. Thus, desired rates of release may be achieved by employing specific polymers, which are preferably cross-linked to a degree affording the desired rate of release. Matrices that are highly cross-linked would release the active material or materials more slowly, and vice versa. The man of skill in the art of pharmacy and delivery system is familiar with such considerations, which are described in many articles and textbooks, e.g., Remington's Pharmaceutical Sciences, Gennaro A. R. ed., Mack Publishing Company, Easton, Pa., 1990, which is fully incorporated herein by reference.

The release of an active agent or agents can be varied within a single matrix or by utilizing a combination of more than one matrix. There are many examples of means for varying release patterns from a single matrix. Examples include different types and degrees of cross-linkage and different additives (such as antimicrobial agents, preservatives, sterilizing agents and enzyme inhibitors) which influence the biodegragation. Furthermore, the release of even a single agent can vary by the manner it is bound in a matrix. For example, sodium fluoride can be released from a single matrix in a biphasic manner where the initial release is of loosely bound sodium fluoride and the next release is of more firmly bound sodium fluoride. Different patterns can also be obtained by using different types of fluoride, for example sodium fluoride, acidulated phosphate fluoride and an amino fluoride, which differ chemically and in molecular size. Another facet is that the matrix can create a microenvironment which excludes some salivary products such as proteins that inhibit mineralization, and others which include mineralization such as calcium phosphate and arginine. The biphasic pattern of sodium fluoride release allows an initial burst of fluoride ions to exchange with hydroxyapatite $OH^-$ groups and accelerate remineralization, then the decrease of fluoride release allows the crystals to grow by providing some fluoride, calcium and phosphate from the matrix. The latter two elements can either be added as agents to the matrix or absorbed by the matrix from the saliva. The final release also favors the deposition of calcium fluoride globules which are long term pH sensitive fluoride reservoirs.

Another approach of varying release patterns is the use of more than one matrix either as separate layers or multilocated systems. Besides causing different release patterns, the use of more than one matrix can keep different agents apart to in situ placement. Each matrix could be loaded with the same or different agent/s that could be released at different rates and/or stages by utilizing intrinsically different matrices at the chemical level or/and physical parameters. For example, the outer layer of a bilayer sphere would first be exposed to the saliva and release, for example, an effervescent cleaning system which loosens and dislodges interproximal plaque and debris and then the inner layer releases, for example, fluoride ions. Another example is the initial release of hypochlorite, which removes organic content of dentinal tubules and then a mineralizing agent or agents. (see Inaba D. et al., Caries Res. 30:218-224 (1996).) Yet another example is that the device can comprise of a coronal and an apical region where the coronal region contains an agent or agents more effective on enamel and the apical region contains an agent or agents more effective on cementum, dentin, gingival and periodontal tissue. An example of a multilayered multi-phase release system is one designed to mimic chiton radula formation which could be used to favorably alter tooth surfaces.

These matrices can comprise a single unit which was affixed one upon the other either by physical pressure or chemical bonding. They can also be formed by plating the first layer and then the same layer is plated over the dried first layer.

The present invention more particularly relates to a retention device for affixing at a dental site within the intraoral cavity, and directed at the chemical treatment of dental surfaces at the site or for chemical and/or physical restoration of the dental surfaces.

Figure 1B:
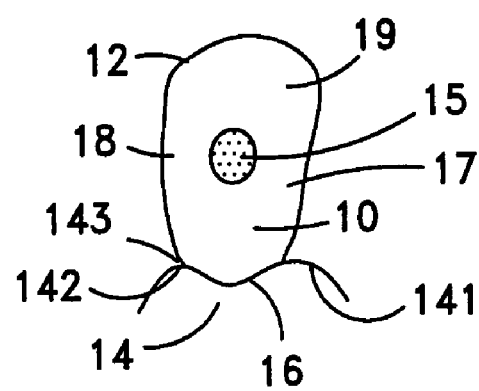
FIG. 1(b) illustrates a cross-sectional view taken along X-X of the embodiment of FIG. 1(a), showing the bicuspid (premolar) with the lingual interdental gingival papillae, the buccal (facial) interdental gingival papillae, the contact area and the gingival col.

Referring to FIG. 1(a) showing a side, elevation view of a lingual portion of a molar (11) and a bicuspid (premolar) (12), and referring to FIG. 1(b) showing a cross-sectional view taken along X-X of FIG. 1(a), an interproximal site (13) is defined herein as comprising both the area of contact (15) which is between two teeth on the medial and distal dental surfaces and the spaces surrounding area of contact (15) on the lingual (17) and buccal (facial) (18) sides of the area of contact (15), as well as at the coronal space (19) and the apical space (10). The apical space (10) is bordered apically by interdental gingival papillae (141) and (142) on the lingual (141) and buccal (facial) (142) surfaces and by a valley known as the col (16), which is the central apical base of the interproximal site (13), and which spans the interdental gingival papillae (14). The apical space (10) also includes the gingival sulcus (143) which surrounds the tooth (12) (see Glickman I Clinical Periodontology $4^{th}$ Ed Saunders pg 18-19). The morphology and size of the above mentioned spaces are determined by the tooth size, position and shape. For instance, the contact area in the posterior teeth is located nearer the buccal surface (18) which causes a larger lingual gingival papilla (141). The contact area in anterior teeth is located nearer the lingual surface, which causes a larger lingual papilla (see Gilmore H W et al, Operative Dentistry, $3^{rd}$ Ed., CV Mosby Company, pg. 25-26). Furthermore, the permanent anterior interdental papillary widths are less than those of the permanent molars which range from about 14 mm to 5 mm. Obviously, primary (milk) teeth also have smaller interdental papillary width dimensions. Additionally, diseases can also cause variations in shape and size. For example, periodontal disease increases the size of the spaces because of gingival and bone loss, however, on the other hand, spaces can be reduced due to gingival swelling.

It should be noted that the contact area is erroneously referred to in conventional literature as a contact point, like two marbles making contact. This is often not the case, since attrition causes the contact to flatten, and the teeth to move, which results in a contact area of about 0.3-1.0 $mm^2$ in the posterior teeth, and smaller areas in anterior and milk teeth. (see Gilmore H W, et al, op cit.)

The term, "dental surface" is defined herein as referring to any portion of a tooth or portion of the gingiva, particularly at interproximal sites and furcations.

The term, "reshape" as used herein refers to the act of reducing the overall dimensions of an object, for instance by bending, folding, rolling or otherwise collapsing the object to a desired configuration (shape), physically or chemically. To that end, the terms, "collapsing", "bending", "folding", "rolling", etc. particularly refer to the reshaping of the device of the present invention to allow the device to fit in an area of a dental site that is smaller in at least one dimension than that of the device in its original shape (e.g. prior to reshaping).

The term, "dental site" as used herein refers in general to interproximal sites and furcations. More specifically, the dental sites referred to herein comprise at least a space between adjacent dental surfaces, such that with reference to the interproximal site, the dental site includes at least a portion of the spaces (e.g. the apical space) surrounding the area of contact, and in some cases, includes the area of contact as well.

According to the present invention, in at least the reshaped configuration, the retention device is preferably shaped in an anatomical configuration according to the contours of the dental surfaces at the sites at which the device is affixed.

Figure 2A:
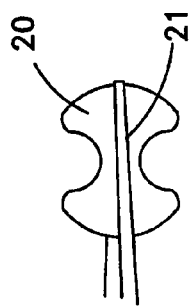
FIG. 2(a) illustrates a first embodiment of the retention device of the present invention in an H-shape.
Figure 2B:
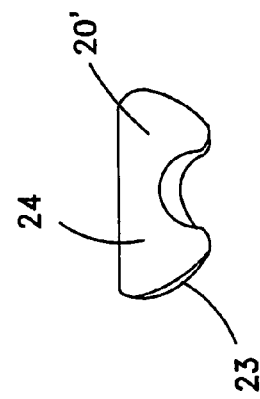
FIG. 2(b) illustrates the retention device of FIG. 2(a) gripped along the centerline of the device by the tip of tweezers.
Figure 2C:
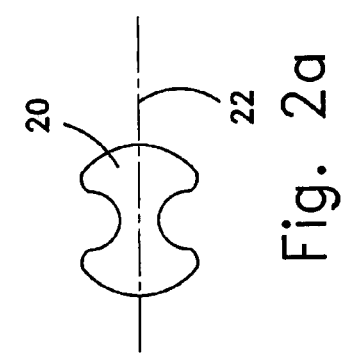
FIG. 2(c) illustrates the direction in which the retention device of FIG. 2(a) is folded while being gripped along the centerline by tweezers.
Figure 2D:
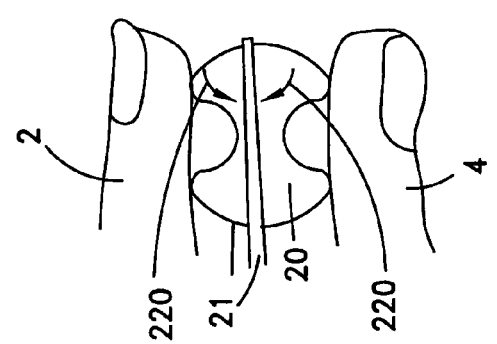
FIG. 2(d) illustrates the retention device in a folded configuration.
Figure 2F:
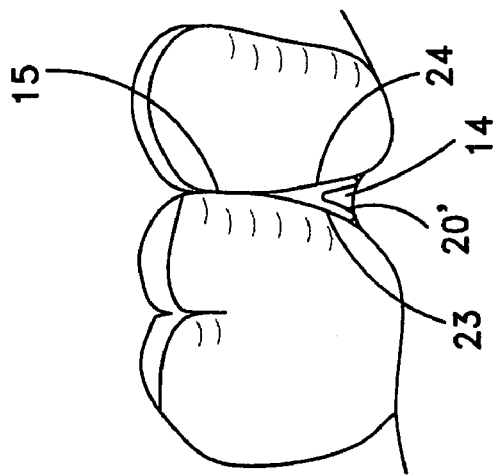
FIG. 2(f) illustrates the folded retention device positioned interproximally.
Figure 2E:
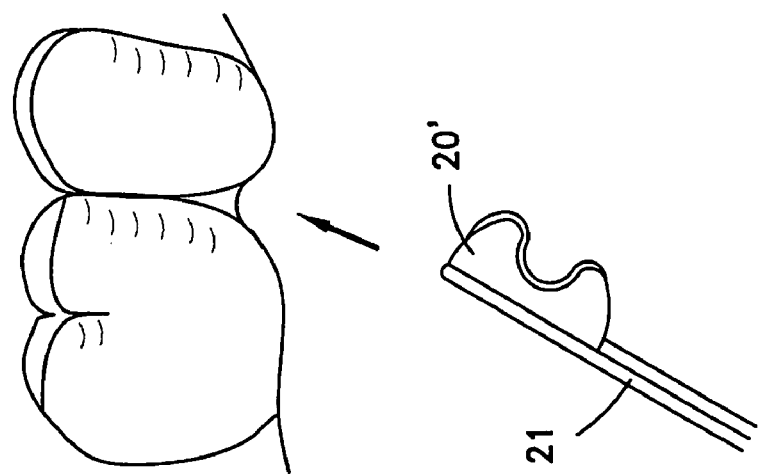
FIG. 2(e) illustrates a side elevation view of a bucal portion of two lower posterior teeth similar to that shown in FIG. 1(a), showing the folded retention device being inserted interproximally while being gripped by tweezers.

Thus, in a first aspect of the first embodiment of the present invention, and referring to FIGS. 2(a) to 2(f), the retention device (20) comprises a polymeric matrix containing an active material, and, in the first aspect, has an H-shape. Retention device (20) is folded as described herein below, for affixing at a dental site, typically below area of contact (15), and in some cases also at area of contact (15), depending on the morphology of the interproximal area, the rigidity of the device and operative procedures. Referring to FIG. 2(b), retention device (20) may be gripped along its longitudinal centerline (or, bending line) (22) (see FIG. 2(a)) by the tip of thin tweezers (21). Since retention device (20) may be stiff (and cracked if bent when dry) tweezers (21) are preferably first dampened, for instance with a water syringe from a dental unit or by dipping into a container of water prior to gripping, to allow retention device (20) to soften along the axis about which the folding is performed. As seen in FIG. 2(c), while gripping retention device (20) with tweezers, (21), the user additionally holds the outer edges of retention device (20) with fingers (2), (4), and applies enough force to fold the outer edges toward each other as indicated by arrows (220), thereby forming two flaps (23), (24), as shown in FIG. 2(d). Preferably, each outer edge is folded inwards to form an angle of approximately 30° between flaps (23), (24), however, retention device (20) may be folded more or less than 30°, and may be rolled or folded over more than once, depending, among other things, on the size of the interproximal site. Referring to FIGS. 2(e) and 2(f), folded retention device (20') is inserted interproximally in an "A" (or, upside down "V") orientation. When fixated interproximally, the apex of the "A" is situated below or at contact area (15) of adjacent teeth (11), (12), and the outer surface of flaps (23), (24) rest along the mesial and distal tooth surfaces. The inner surface of flaps (23), (24) arch over gingival (14). When absorbing the moisture and fluids in the intraoral cavity, the device softens and expands in situ, thereby causing device (20') to essentially fill all or some of the space of the interproximal site (13).

FIGS. 3(a) and 3(b) show the first aspect of the first embodiment, wherein the retention device (20") is in a rolled configuration for physically affixing in a furcation (33) using a tweezer. FIG. 3b shows rolled device HH physically fixed in the furcation (33) of the molar. When absorbing the moisture and fluids in the intraoral cavity, the device softens and expands in situ, thereby causing device (20'") to essentially fill all or some of the space of the furcation (33).

Figure 4E:
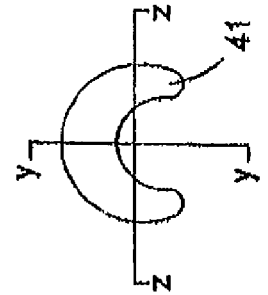
FIG. 4(e) illustrates the retention device in a C-shaped configuration, showing the axes about which the device may be folded to form a symmetrical (Y-Y) shaped device or asymmetrical (Z-Z) shaped device.
Figure 4B:
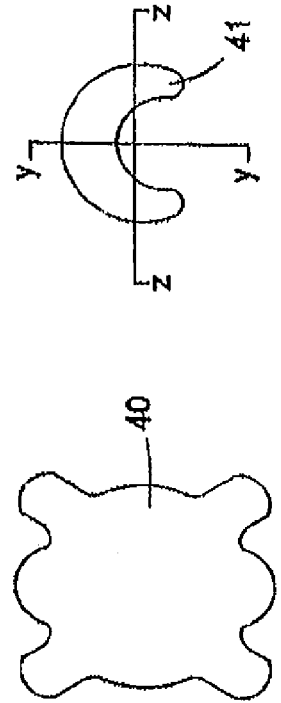
FIG. 4(b) illustrates the retention device similar to that shown in FIG. 4(a), in an elongated form to fill an assymetrical col area.
Figure 4D:
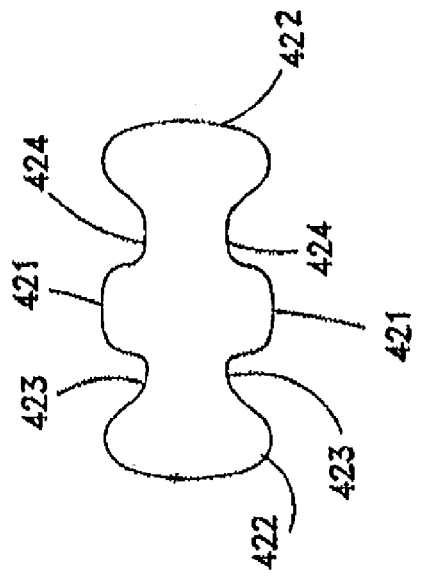
FIG. 4(d) illustrates the retention device in a star shaped configuration, similar in essence to that of FIGS. 4(c) and 4(d).
Figure 4A:
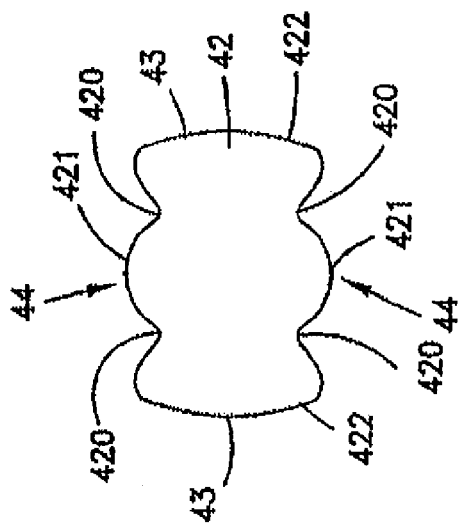
FIG. 4(a) illustrates the retention device a configuration comprising notches (or, recesses) to facilitate interproximal placement around the interdental gingival papilla, and extensions (or, protrusions) in order to fill the col area and to overlap the gingival papilla on the exterior portions.

A second aspect of the first embodiment is shown in FIG. 4(a), in which retention device (42) is shaped according to the contours of the apical space of the interproximal site, Retention device (42) comprises slightly convex transverse edges (43) (although straight or concave edges may be desirable in some cases), and longitudinal edges (44) comprising notches (or, recesses) (420) to accommodate the interdental gingival papilla, and extension (or, protrusions) (422) to enhance retention at the dental surfaces, and a central extension (421) to fill the col area and also enhance retention. Alternatively, extension (422) may be excluded, elongated or shortened, and the cross-sectional shape need not be straight but can be concave on one or both surfaces. Alternative shapes for conforming to the anatomy of different dental surfaces (e.g. interproximal sites) may be desired. For example, anterior and posterior spaces differ in size and in shape from each other. Specifically, the posterior areas are wider, the position of the col is not at the midpoint, and the buccal and lingual gingival papilla are not the same size. FIG. 4(b) illustrates an alternative aspect of the second aspect, wherein notch (424) is elongated to conform to the anatomy of posterior teeth interdental gingival papillae.

Furthermore, the second aspect can comprise the apical and coronal portion differing in shape. For example, the coronal portion can be straight or dome shaped and the apical portion can be anatomically shaped, like that of FIGS. 4(a)-4(d).

Figure 4C:
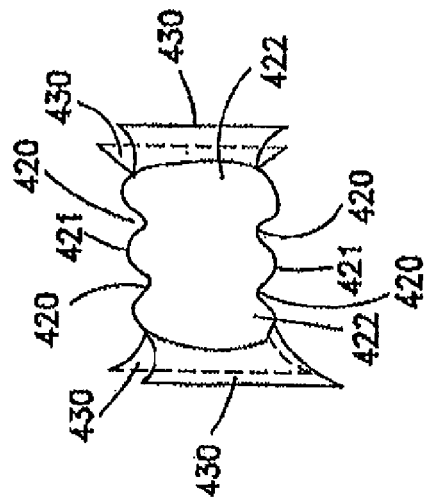
FIG. 4(c) illustrates the retention device shown in FIG. 4(a) with side flaps (or, wing members) which also facilitate retention at an interproximal site and increases the area of contact of the device to a larger area around the contact area.

FIG. 4(c) shows the second aspect of the first embodiment, wherein the retention device has wing members (430) for contacting the buccal and lingual tooth surfaces. Alternative structures may be used instead of wing members to facilitate retention at the interproximal site, and increase the contact of the retention device to a larger area around the contact area.

FIG. 4(d) shows a third aspect, wherein retention device (40) is shaped in a star-shape, which is essentially similar to the embodiment shown in FIG. 4a, but with concave edges, instead of convex edges, and which may be reshaped for affixing at a dental site; FIG. 4(b) shows a fourth aspect, showing a C-shaped retention device (41) which can be folded, for example, along Y-Y to form a symmetrically folded device, or along Z-Z to form an asymmetrically folded device. Other variations (not shown) include a star-shaped device that is elongated (i.e. stretched) in at least one plane.

Preferably according to all aspects of the first embodiment, retention device is designed to facilitate bending or folding. For example, the bending line may be indented along the entire length, or indented or punctured at intermittent points or lines (i.e. perforations) across at least a portion of the length of the bending line. Alternatively, a marking such as a line may be situated along the surface of the retention device to indicate the preferred axis about which retention device should be folded, for instance, in order to form the desired flaps. This line can be a physical form of an area which has been chemically treated to facilitate folded.

The present invention includes other aspects not shown in the figures or described herein, such as a palette shape (see U.S. Design applications Ser. No. 29/234,883 by the present inventors). Furthermore, the surfaces of the device may be flat, or one or more surfaces may be concave or convex, or any combination thereof of shapes.

Figure 5B:
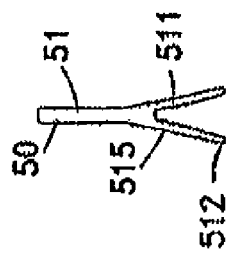
FIG. 5(b) illustrates a cross-sectional view of the embodiment of FIG. 5(a) taken along line XX-XX.
Figure 5A:
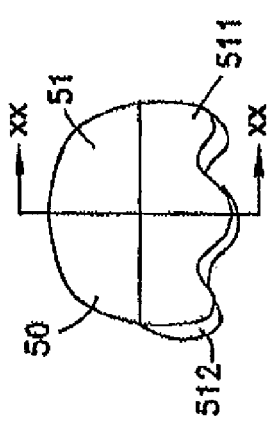
FIG. 5(a) illustrates a front view of the retention device in a Y-shape in an upside down orientation, which is anatomically contoured at the two apical portions, and slightly concaved at the portion for positioning at the contact area.

A second embodiment of the present invention, comprising all of the advantages and features of the first embodiment, mutatis mutandis, is shown in FIGS. 5(a)-5(d), with the following differences. As seen in the figures, particularly FIG. 5(b) showing a cross-sectional view taken along XX-XX of FIG. 5(a), retention device (50) is Y-shaped, for inserting and affixing in an upside down orientation at an interproximal site (FIG. 5(c)) such that the elongated portion (51) is disposed at contact area (513), and the "A" portion (515) is disposed beneath contact area (513) of adjacent teeth (52), (53), wherein flaps (511), (512) contact adjacent dental surfaces. Flaps (511) and (512) are designed to be bent slightly towards one another in order to be placed interproximally, whereafter flaps (511), (512) press slightly away from one another towards adjacent dental surfaces, thereby enhancing fixation of retention device (50) at the interproximal site. Included in this embodiment are modifications of the above description, for example, a device that only incorporates the "A" portion (515), without elongated portion (51).

Figure 5D:
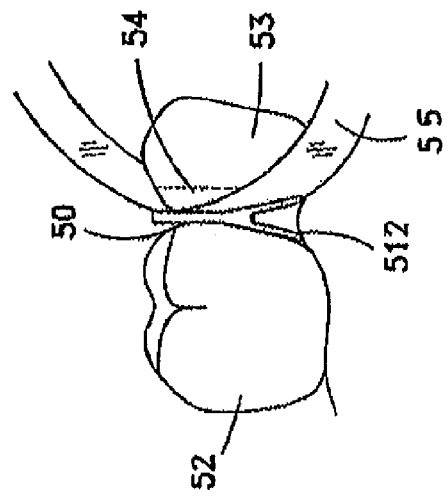
FIG. 5(d) is a side elevation view similar to FIG. 1(a) showing a matrix band being held in situ by a Y-shaped retention device between the molar and bicuspid (premolar) in order to facilitate restoration of the cavity.
Figure 5C:
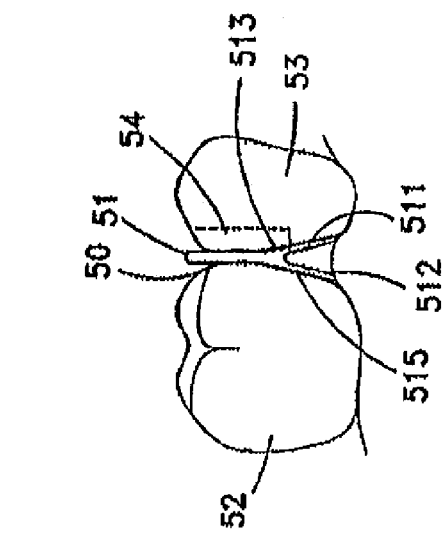
FIG. 5(c) is a side elevation view similar to FIG. 1(a) showing the device of FIG. 5(a) in situ—between the molar and bicuspid (premolar), which has a distal cavity in the bicuspid that requires a restoration.

According to one aspect of the second embodiment of the present invention and referring to FIGS. 5(c) and 5(d) retention device (50) can be made of a metal or plastic material for fixation at an interproximal site, in order to facilitate the restoration of a cavity (54) with an appropriate restoration material such as a tooth colored resin, glass ionomer or amalgam, independently, as shown in FIG. 5(c) or with a matrix band (55) as shown in FIG. 5(d). When flaps (511) and (512) push towards adjacent dental surfaces as described above, retention of matrix band (55) is facilitated.

A third embodiment of the present invention, comprising all of the advantages and features of the first and second embodiments, mutatis mutandis, is shown in FIGS. 6(a)-6(c), with the following differences. The third embodiment comprises a system of folded retention devices (62) attached directly or via at least one short or long extension arm (64) to an elongated strip (61) having the form of at least a portion of an entire dental arch, to allow a plurality of devices to be essentially simultaneously inserted to a dental site. FIG. 6(b) shows a cross-sectional view taken across line YY-YY of FIG. 6(a), showing strip (61) covering the facial portion of anterior teeth (63). FIG. 6(c) shows a top view of a strip (65) corresponding to an entire dental arch.

These applications are not limited to devices of a biodegradable, resorbable or non-resorbable nature nor any combination thereof which are left in situ, but include devices that are activated or influenced by external means such as chemical or physical intervention. This forms a tough solid device at the site. An example of a physical application such as laser irradiation using $CO_2$ lasers, Nd:YAG lasers and Argon lasers.

The physical affixing of the device of the present invention is by way of a physical property of the matrix, in particular wherein the matrix comprises a hydrophilic polymer which softens and swells in situ by the hydration thereof in the oral cavity after accommodation at the dental site. The expansion can be designed to thicken (e.g. to 250%) in size substantially more than it elongates (e.g. 20%), thereby not extruding excessively out of the interproximal and tooth domain. Optionally, the retention device comprises at least one adhesive surface or part thereof such as to enable the system to adhere or be fixed at a dental site.

Again, of course this invention is not limited to the above-described embodiments, but encompasses all the variations thereof. It is also obvious to those schooled in the art that general toxicity, allergic responses and pulp responses need to be investigated prior to applying the proposed techniques clinically.

In the system according to the present invention, the oral activity provided by the active material or materials may be medical treatment such as fluoridization, remineralization or mineralization and desensitization and/or aesthetic treatment such as tooth whitening or providing breath fresheners, and/or any other desired activity.

Thus, the different components of the matrix of the invention can comprise a range of chemicals with the following functions:

The Primary Active Fluoridating Mineralization and/or Remineralization Agents

The fluoride releasing agent/s and other mineralizing and remineralizing agent/s can be embedded within the polymeric matrix or matrices of the invention, and released from there in a controlled or sustained manner with or without at least one auxiliary chemical or physical step for example electrodes, sonification or laser application to the device in situ. The matrix or matrices described in this invention may comprise at least one primary active fluoridizing mineralization and/or remineralization agent which provides fluoride and/or other ions, which primary agents can be divided into fluoridating agents and other mineralizing and/or remineralizing agents.

Fluoridation Agents

This agent may be any single or any combination of inorganic or organic fluoride-containing pharmaceutically acceptable chemicals known or to be developed. These include, but are not limited to amine fluorides, e.g. olaflur [($N^1$-octadecyl-trimethylendiamine-N,N,N tris (2-ethanol)-2,2'-(3-n-(2-hydroxytheyl)octadecylamino]propyliminol)dihydrofloride] and dectaflur (9-octadecenylamine-hydrofluoride)), alexidine dihydrofluoride, hydrofluoride, ammonium fluoride, calcium fluoride, calcium carbonate monofluorophosphate, difluorosilane, fluoroaluminosilicate glass and any mixture thereof, hydrogen fluoride, fluoropolymer B (see U.S. Pat. No. 4,837,007), mixed salt neighborite (NaMgF3), magnesium fluoride, magnesium monofluorophosphate, potassium fluoride, lithium fluoride, indium fluoride, zirconium fluoride, copper fluoride, nickel fluoride, palladium fluoride, potassium fluorozirconate, tin fluorozirconate, sodium fluorozirconate, ammonium fluorozirconate, fluorosilicate fluorozirconate, fluoroborates, fluorozirconate, fluorostannites, fluorozirconate, sodium fluoride, stannous fluoride, stannous hexafluorozirconate, sodium hexafluorosilicate, sodium, lithium or potassium monofluorophosphate strontium fluoride and ytterbium trifluoride. Preferably, the active mineralisation agent is sodium fluoride, and/or hydrogen fluoride. This invention is not limited to the above but includes approaches such as the corporation of fluoride in the form of $Ca_5(PO_4)_3F$ (see U.S. Pat. No. 4,556, 561). Variations in pH and salt types of fluorides (e.g. stannous, ammonium, titanium and amino fluorides) result in different retention of fluoride as calcium fluoride. For example, good results have been obtained using fluoride at lower pH values such as ammonium fluoride (see Jenkins, G. N. The Physiology and Biochemistry of the Mouth p. 495, 1978, Blackwell Scientific Publishing) and preferably thixotropic acidulated phosphate fluoride which can contain about 1-4% sodium fluoride with or without 0.1-0.8% hydrogen fluoride and 0.5-1.5% orthophosphoric acid (see Craig, R. G. et al Dental Materials, Properties and Manipulation p2-28, $2^{nd}$ Ed 1979 CV Mosby Co.)

The period of fluoride exposure which causes significant rehardening of a demineralized enamel surface is about 4 hours (see Koulourides, T., Art and Science of Dental Caries Research pp. 355-378, 1968; Poole, D. F. G. and Silverstone, L. M., Hard tissue Growth Repair and Remineralisation, pp. 35-52, Ciba Fondation Symposium No. 11, Elsevier Scientific Publishing Company, 1973, Pearce E. I. F and Moore, A. J., J. Dent Res 64;416-421, 1985). Obviously the period of fluoridation required is dependent on the type of material or device herein described, its fluoride type and concentration, frequency and period of delivery, other chemical or physical interventions (such as current and laser application) and the type of surface or lesion being treated. Furthermore, the effects can also be long term because of the deposition of pH controlled fluoride reservoirs of various $CaF_2$ forms.

The acute lethal dose of fluoride (F) is 33 mg F/Kg body weight and the chronic toxicity can be 0.1 mg F/Kg. Thus the determination of the fluoride concentration range is governed by the size and number of devices used or the volume of material used, the duration of applying the material or device, the rate of fluoride ion release and the weight of the patient. Thus the concentrations can range from about 7-0.2%. (See: A guide to the use of fluorides JADA 113:504-564, 1986, prepared by the National Fluoride Task force of the NFDH).

Mineralizing and/or Remineralizing Agents

Although fluoride is to date the most effective remineralization agent, this invention and practice thereof is not limited to fluoride alone but may include or be limited to any other mineralizing or remineralization agent known or to be developed or combination thereof. Examples are amorphous minerals, crystalline minerals and organic molecules.

An advantage of amorphous minerals is that they can be easy to mold into complex shapes (see Levi-Kalisman, Y. et al J. Chem Soc. Dalton Trans 2000: 3977-3982, 2000) such as pits and fissures, demineralized enamel or dentin. These amorphous minerals can be present in stable or unstable phases. Silica (opal) is a stable type which can be formed by the polymineralization of silicic acid which can be mediated enzymatically. On the other hand amorphous calcium carbonate and amorphous calcium phosphate are unstable as they tend to transform into stable crystalline phases. Amorphous calcium phosphate, amorphous calcium phosphate fluoride, amorphous calcium carbonate phosphate, casein phosphopeptide, amorphous calcium phosphate nancomplexes, amorphous calcium carbonate phosphate fluoride, and amorphous calcium fluoride have high solubilities, fast formation rates and fast conversion rates to apatite (see U.S. Pat. No. 5,460,803). This transformation can be controlled, for example by mimicking chiton teeth where amorphous calcium phosphate is converted into dahllite. Besides these agents there are other agents such as dicalcium phosphate dehydrate which complement fluoride in remineralizing carious lesions (Wefel, J. S. and Harless, J. D. J. Dent Res 66: 1640-1643, 1987, Takagi, S. et al Caries Res 34: 281-288 (2000)).

Examples of crystalline minerals are aragonite, brushite (see U.S. Pat. Nos. 3,679,360 and 5,605,677), calcite, dahltite, ferrihydrite, fluoroapatite, hydroxyapatite (which can also be used in dissolved synthetic forms) or in a stannous hydroxyapatite fluoride (see U.S. Pat. No. 4,923,683), lepidocrocite, magnetite, octocalcium phosphate, vaterite and whitlockite. This invention also includes a system designed to alter a tooth surface thereby enhancing its resistance to caries and other pathology. For example the process of chiton radula formation can be fully or in part adapted to alter tooth surface clinically. For example iron atoms can be introduced which precipitate a hydrated iron-oxide mineral, ferrihydrite which can then be converted to magnetite or an iron oxide mineral, lepidocrocite. Another example is amorphous calcium phosphate which can be deposited and then induced to crystallize to dahllite or hydroxyapatite (see Addadi, L. and Weiner, S. Angew, Chem. Int. Ed. Engl. 31:15, 3-169, (1992). Besides hydroxyapatite, an often found mineral at remineralized or mineralize dental sites is whitlockite (Kodaka, T. et al Caries Res 26: 69-76 (1992). These amorphous or crystalline minerals can be used to restore demineralized tissue such as interproximal caries or to seal regions such as pits and fissures by chemical or physical intervention (such as laser application), to seal areas or alter the chemical surfaces thereof.

The organic material can be macromolecules such as acidic proteins, glycoproteins and sulfated polysaccharides (Addadi, L. and Weiner, S. Angew, Chem Int Ed Engl 31:153 169, (1992)) or smaller molecules such as polyaspartic and polyglutamic acid with or without a rigid substrate adsorption (Addadi, L. et al ACS Sym. Series no. 444, 1991).

Enhancing or Other Active Agents

These agents can be the matrix or part thereof or added to the matrix (e.g. silated hydroxyethylcellulose as apatite is formed because silanol chelates calcium (see Turezyn, R. et al J. Biomater Sci. Polym Ed 11:217, (2000)) polyampholyte-sodium fluoride and chlorhexidine (Wefel J. S. et al. Am J. Dent. 8, 217-220 (1995); Caufield, P. W. and Navia, J. M. in the Biological Basis of dental caries, Menaker, L. 406-407, Harper and Row, (1980), benzoate-like preserving agents (see Davis, B. A. et al Caries Res 35, 331-337, (2001), Isomalt® (Takatsuka, T. J. Dent Res. Sp Iss. A #2815 (2002), silanols (see Loty C et al J. Biomed. Mat. Res. 47; 367 (2000), and dicalcium phosphate dihydrate calcium carbonate (see U.S. Pat. No. 4,556,561 and Cury, J. A. et al Caries Res. 183 (2003). Calcium and phosphate are another example (ideally 1.5 m mol/L Ca and 0.9 m mol/L PO4) see Exterkate, R. A. M. et al J. Dent Res. 72 1599-1603 (1993). Examples of suitable calcium compounds are: calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium maleate, calcium maleate, calcium propionate calcium vaerate. Examples of suitable inorganic phosphates are alkali salts and ammonium salts of orthophosphoric acid such as potassium sodium or ammonium orthophosphate, monopotassium phosphate, dipotassium phosphate tripotassium phosphate, monosodium phosphate, disodium phosphate and trisodium phosphate. Other active agents are (e.g. sodium lauryl sulphate (to reduce surface tension), azacycloheptane, diphosphonate, triclosan, polyvinyl methylether with maleic anhydride copolymer resins (see Zhang et al J. Clin. Dent 14: 23-28 (2003) xylitol, erythritol, vitamin E, aloe vera and rigid beta sheet proteins such as synthetic polyaspartate and polyglutamate proteins and natural agents purified from mineralized tissue such as glycoproteins phosphorylated amino acids and acidic sulfated polysaccharides (see Addadi et al ACS Symposium series 444; Addadi et al in Chemistry and Biology of Mineralized Tissues, Ed. Slavkin, H. and Price, P. Elsevier Sci. Pub. BV 153-162 (1992)), acidic macromolecules associated with hydrophobic macromolecules such as type 1 collagen, alpha and beta chiten (see Addadi, L. and Weiner, s. Angen. Chem. Int. Ed. Engl. 31: 153-169 (1992)) and other molecules and substances such as arginine, silk and elastin. They can also be inorganic agents such as zirconium and ferric pretreatments (see Clarkson B. H. et al. J. Dent. Res. 60:1912-1920 (1981) or organic solvents such as urea designed to clean the carious lesion (see Shellis, R. P. et al Eur. J. Oral Sci 110: 392-395, (2002), being part of the system described within the invention or they can be applied prior to the device application. Other agents can be commercial cocktails such as GC Tooth Mousse Recaldent™ or experimental cocktails such as synthetic enamel preparations.

Acidifying, Buffering or pH Regulating Agents

At least one agent can be included in the matrix or matrices to enhance fluoridation, mineralization or remineralization by altering the pH (3-7) (e.g. acidulated phosphate fluoride (derived from sodium fluoride acidulated with a mixture of sodium phosphate monobasic or dibasic, and phosphoric acid or from sodium fluoride, hydrogen fluoride and orthophosphoric acid), $H_3PO_4$, citric acid, sodium citrate, or sodium bicarbonate or by inducing buffering with for example calcium carbonate, arginine and polyacrylic acid fully neutralized with alkali metal ammonium or (alkylol) amine compound sodium polyacrylate (see U.S. Pat. No. 6,106,811). Furthermore, buffers may be required to enhance cross-linkage of the matrix or matrices (e.g. phosphate buffers at pH 6.8). Those knowledgeable in the art will know that more than one stage of buffering may be required prior to the production of the final product in order to facilitate required steps such as cross-linking or curing, and optimal pH of the final device which can be low 3-4 for optimal fluoridation remineralization or mineralization or neutral in order not to etch porcelain and tooth colored restorations. Agents which influence pH can also have important roles such as in the case of the remineralization of dentin which have been reported to only occur after the extraction of proteins (see Clarkson, B. H. et al Caries Res 32: 357, 1998). Thus, the matrix or matrices could contain for example lactic acid, acetic acid, phosphoric acid or EDTA in a single matrix or on an external surface layer of a bi or multilayer device. On the other hand the dentin or enamel could be first primed with such agents using a liquid gel or an etching device, whereby the active agent is an acid, for example 37% phosphoric acid. Such a device could also be used to etch tooth surfaces prior to bonding of dental material. Another type of device could contain both the etching and bonding agent which is activated and/or cured, for example by water and/or light application (I.R., U.V. visual spectrum or lasers). One side of an interproximal device could be inactive and the second side could be an active site which could be used to fill, seal or coat interproximal sites, fissures, pits, lesions, caries, restoration defects or restoration-tooth margin defects. This second side could be a single phase or double phase system.

Another novel approach is the introduction of a buffering agent such as sodium bicarbonate during remineralization which penetrate into the subsurface lesion and then function as a buffering agent during acid challenges (see Tanaka, K. and Iijima, Y. J. of Dent. 29: 421-426 (2001)).

The Matrix and Cross-Linking Agents

The role of the matrix or matrices is to carry at least one primary active fluoridation mineralizing or remineralizing agent with or without at least one enhancing agent or other active agent and to provide the required viscosity, strength, plasticity and elasticity for application as well as the required stability or degradation pattern for the delivery of the active and any auxiliary agents, in order to provide the optimal rate and time span of ion or chemical interaction with the tooth surface and to provide a mobile environment for the appropriate ions and/or other chemicals to reach the tooth surface. Those knowledgeable and skilled in the art can alter the degradation by varying the concentrations and the degree of curing or cross-linking and type of cross-linking, or combinations thereof as well as the concentration and types of enzyme inhibitors, antimicrobial agents, preservatives and sterilizing agents which can interfere with intra-oral biodegradation. Some degradation properties may not be required in a matrix or part thereof if specific chemical or physical intervention requires instantaneous delivery.

The types of possible matrices are wide. They can include agents yet unused for dental treatment and agents such as those used as denture adhesives, impression materials, temporary, provisional or permanent restorations, sutures, perio- or surgical packs and periodontal agents (see Dental Therapeutics Digest Odontos Pub Inc.: Kay L. W. Drugs in Dentistry, Bristol 1972; O'Brien, W. J. and Ryge, G. An Outline of Dental Materials, Saunders 1978; Steinberg, D et al., J. Dent. Res. 67-208 Abstract No. 767, 1988; U.S. Pat. Nos. 5,324, 519, 4,938,763, 5,278,201, 5,077,049, 5,739,176 and 5,733, 950). The matrix or matrices material or materials may be sub-classified into natural products and synthetic products.

Polysaccharide polymers (e.g. agar, alginates, carboxymethylcellulose, carrageenan, cellulose, gellan gum, Kelcogel®, Kelcogel®F, Kelco Biopolymers, starches and retted flax extracts), lipids, polyisoprenes (e.g. latex rubber and gutta percha), resins and gums (e.g. tragacanth and storax) and proteins (e.g. alpha or beta chitin, soluble elastin and collagen or denatured collagen in the form of gelatin) are examples of natural products. In some cases agents may need to be treated, for example, dialyzed and de-ionized to remove impurities.

Purified collagen can be untreated or treated with fixing agents to prolong its resistance to digestion (similar to catgut surgical suture production). Denatured collagen can be impregnated with chromium salts to enhance its tensile strength and retard its absorption. A preferred polymeric matrix is a gelatin matrix, although those experienced in the art know the method of dissolution of gelatin is highly technique-sensitive and the method used can cause considerable differences in the texture. Further, gelatin, like collagen, can be lysine-cross linked with glutaraldehyde (an organelle preservant which has also been used for human aortic valve implants and dental pulp treatments; Kopel, H. M. et al., J. of Dent. for Child 47: 425-430, (1980)) and Periochip®. Another possible cross-linking agent is formaldehyde, which forms intra- and intermolecular methylene bridges between various amino acids. Further examples include but are not limited to allyl methacrylate, 2,3- or 3,4-dehydroxybenzaldehyde, glycol dimethacrylate, nordihydroguaiacetic acid, rosemarinic acid, strontium, calcium, tannic acid and hexamethylenediisocyanate and chondroitin sulfate. Again, the biocompatibility of these agents must be carefully examined even though some of them have been used clinically. Physical means of treating gelatin to induce cross-linking are also possible for example by microwave-treatment (Vandelli, M. A. et al J. of Controlled Release 96,67-84 (2004)). The gelatin may be of any source, for example bovine or non-mammalian gelatin. Bovine gelatin is preferably used when a matrix or matrices with higher rigidity is required.

It is prudent to note that a completely natural matrix of gelatin without cross-linking can also be used with an appropriate cover. Furthermore, natural cross-linkings are also feasible, for example calcium and hydroxylysin or leucine, dihydroxylysine or leucine (Traub W., and Piez, K., A. Adv. Protein Chem. 25:243-352, 1971), lysine, arginine, proteins, polysaccharides such as dextran, lipids such as sodium docusate and dehydrodihydroxylysine or leucine (Bailey, A. J. et al., Biochem. Biophys. Res. Commun. 35:663-671 (1969)), and enzymatic cross-linking, for example, by transglutaminase (Orban J. M. et al. J of Biomedical Materials Research 68A:756-762, (2004)).

Likely candidates within the boundary of possible synthetic products that may serve for the matrices of this invention are homopolymers or copolymers with a wide molecular weight range formed by condensation, additional anionic, cationic and/or catalytic polymerization systems. Examples are acrylamide based polymers and a cationic monomer (see U.S. Pat. No. 4,837,007) cyanoacrylates, polycarbonates, polyurethane, polyester urethane dimethacrylate, polycaprolactones, ethyl triglycide methacrylate, polysulphides, povidone, polyacrylic methacrylic acid, acrylic and modifications such as poly(hydroxyethyl methacrylate), poly(methylmethacrylate) modified with small amounts of ethyl butyl or other alkyl methacrylates, polyethylene glycol, sodium polyacrylate PEG 400 and PEG 3350 and other carbomers. Some of these are indeed commercial or laboratory products such as polymethylvinylether-co-maleic anhydride and polyvinylether-co-maleic anhydride and polyvinyl pyrrolidone, carboxymethylcellulose, silated hydroxyethylcellulose or hydroxypropyl methylcellulose (Bourges et al Adv. In Colloid and Interface Sci 215-228: 2002; Bourges X. et al. Biopolymers 63:232-238: 2002) aqueous methacrylic polymer formulations for sustained and controlled release of dental and other products (e.g. Eudragit® Rohm). These polymers may require activators and cross-linking (see below). However, other agents are at times required, for example retarding agents such as hydroquinone and eugenol. Other yet different examples are zinc eugenolate, petrolateum and stearyl alcohol. Other gels may be included such as Carbopol polymers. (BF Goodrich Noveon) or a Na2Si O39H 2 0 solution mixed with phosphoric acid and hydrofluoric acid (see U.S. Pat. No. 3,679,360).

It is to be appreciated that the degree of cross-linking is of major significance to the rate of release of the active and/or auxiliary agents. The determination of the degree of cross-linking of the polymeric matrix or matrices is within the capabilities of the man of skill in the art of pharmacy. Other factors are antimicrobial agents, preservatives, sterilizing agents inhibitors (such as inhibitors of matrix metalloproteinases (see WO 98/16503) and enzyme inhibitors which slow down the biodegradation of the matrix or matrices.

The matrices of the present invention can be strengthened not only by cross-linking, but also by other methods. For Example, U.S. Pat. No. 6,565,960 describes polymer composite compositions in which the polymer fibers, e.g. collagen fibers and gelatin, are strengthened by adding particular catechol-containing compounds, particularly compounds which have two or more catechol groups, to the polymeric material and forming a polymer of the compounds that intercalate within the polymeric material, e.g., forming a polymer composite. According to this U.S. patent, it is possible that the resulting polymer forms a scaffold-like structure throughout the polymeric material without the necessity of cross-linking the individual polymeric materials, e.g., collagen or gelatin polypeptides. This scaffolding provides synthetic polymer fibers having a tensile strength, stiffness, and strain at failure that is comparable to or better than natural polymeric material fibers. As all references cited herein, also U.S. Pat. No. 6,565,960 is fully herein incorporated.

Other novel matrices which can also be used as matrix and sealing agents, for example at pit and fissures, are Sn—Sn catenation, Sn—Cl chains or lattices or Sn protein chains (see Jodaikin, A. and Goldstein, S., J. Dent. 16:140-144, (1988)), and even combinations with fluoride, calcium, phosphate and tin (see Harris, N. O. and Christen, A. G. Primary Preventive Dentistry $4^{th}$ Ed Norwalk Appleton Longe 1995; Wu. H. et al ,abstract from Hua Zi Kou Qiang Yi Xue Za Zhi 18: 219-221, (2000)).

Yet another novelty is a matrix or matrices which is or includes a matrix-bound fluoride ion exchange system which can be 'recharged' with fluoride from external sources such as toothpastes, oral rinses, dental materials (see U.S. Pat. No. 5,639,840) and professionally applied fluoride systems (see Zimmerman, B. F. et al J. Dent. Res. 63:689-692 (1984); Fuji 1X GP® fast by GC Inc.).

Although the matrix or matrices are defined as a delivery system, this invention does not preclude the use of the matrix or matrices itself as a template or framework to control remineralization or mineralization based on control and design principles culled from biological mineralization or fabricated synthetic analogs.

Preservatives and Sterilizing Agents

The addition of preservatives and sterilizing agents may be advantageous particularly for long-dwelling matrices, as they will inhibit the development of various microorganisms such as bacteria, fungi and yeast, and they could play a role in inhibiting the biodegradation of the matrix or matrices, thereby influencing its longevity and the release of the active agent. Examples of preservatives are benzoic acid, biguanide, polyamino propyl biguanide, cetyl pyridinium chloride, phenol, methylparaben, metal proteins (see Horman, H. in Sigel, H. Metal Ions in Biological Systems Vol 3 New York Marcel and Dekker pg 105, 1974 and Jodaikin, A. and Goldstein, S. J. Dent 16:140-144, (1988)), and sodium bicarbonate, sorbic acid, thymol and examples of sterilizing agents are iodine, potassium and alcohol.

Stabilizing Agents

The purpose is to inhibit an unwanted or premature reaction such as reactions of calcium phosphate and fluoride by chemical means or physical means such as the use of a varnishing, coating or encapsulation agent.

Antimicrobial Agents

Included agents for therapeutic functions can be antibacterial, antiviral, antifungal and other antimicrobial agents. Indeed stannous fluoride has shown antibacterial activity (see Paine, M. L. et al JADA 129, 6977, (1998)). Other examples are alexidine, chlorhexidine digluconate, hexetidine, copper zinc citrate and stannous pyrophosphate, triclosan, cetylpyridinium chloride and halogenated bisphenolec compounds.

Cleaning Agents

The invention can function as an interproximal site cleaning system as an alternative or supplement to flossing. The invention would thus need to include agents such as a surfactant or sudsing agent which foam throughout a wide pH range. Examples of cleaning agents are sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium lauryl carboxylate, sodium dodecyl benzenesulfonate, poloxamers, polyoxyethylene sorbitan esters, fatty alcohol ethoxylates, polyethylene oxide, cocamidopropyl betaine, hydrogen peroxide, sodium bicarbonate, monosodiumphosphate, sodium hydroxide, potassium hydroxide, sodium carbonate and imidazole. Another possibility is effervescing agents of systems such as the use of a sodium bicarbonate/citric acid system. The effervescing loosens or dislodges interproximal plaque and debris at a microscopic level thereby overcoming flossing which cannot negotiate rough surfaces, especially at the microscopic level.

Tooth Desensitizing Agents

Examples are fluorides (see above), potassium citrate, potassium chloride, potassium tartrate, potassium bicarbonate, potassium oxalate and potassium nitrate.

Whitening or Bleaching Agents

Although Whitestrips® by Crest have been marketed as a tooth whitening system in the form of a strip which contains hydrogen peroxide this invention includes a system to whiten difficult areas to access such as interproximal regions. The agents that can be used include hydrogen peroxide, carbamide peroxide, metal chlorites such as calcium chlorite, barium chlorite, magnesium chlorite, lithium chlorite, sodium chlorite, potassium chlorite, hypochlorite, perborates, percarbonates, peroxy acids, persulfates, urea peroxide, calcium peroxide, chlorine dioxide, sodium percarbonate, oxones, and even enzymes such as protease (see U.S. Pat. No. 6,521,215). Stabilizing agents may also be required, for example dipicolinic acid or sodium stannate for peroxy bleaching agents.

Gingiva and Periodontal Agents:

Agents listed in any of the above categories, antimicrobial and cleaning agents can be included, especially chlorhexidine digluconate and hydrogen peroxide (the latter can be combined with baking powder). Other examples are hyaluronic acid, thymol, doxycycline, and tetracycline hydrochloride.

Anticalculus Agents

Examples are alkalimetal pyrophosphates, hypophosphite-containing polymers, organic phosphonates, and phosphocitrates. Indeed some anti-calculus agents could enhance anti-caries activity and improve fluoride availability (see Zhang, Y. P. et al J. Clin. Dent 14: 23-28, (2003)).

Hemostatic Agents

This category includes vasoconstrictors (e.g. adrenalin), absorbable agents (e.g. oxidised cellulose, fibrin, calcium alginate), thromboplastic agents (e.g. thrombin), chemical agents (e.g. aluminum chloride, tannic acid, ferric chloride, ferric sulphate zinc chloride, alum, hyaluronic acid hydrogen peroxide) or physical plugging (e.g. the device includes bone wax). The role of a hemostat would be to stop bleeding which could hamper fluoridation or chemical treatment in regions where bleeding is caused by gingival or other bleeding.

Liquid Vehicles

Liquid vehicles may be solvents used particularly when preparing the matrix or matrices or to facilitate application.

Examples are water, polydimethylsiloxane, ethyl alcohol or glycerin (glycerol) alone or in any combination.

Plasticisers and Elasticisers

Plasticisers and elasticisers may be used to modify the mechanical properties of the matrix or matrices, where needed and desired. Examples are polyethylene glycol, dibutyl phthalate, glycerol, sorbitol, mineral salts, olive oil, linseed oil, light mineral oil, polymers of ethylene propylene, polyolefins, polyacrylates polymethylates, styrene-butadiene, vinyl ethylene acetate copolymers, butadiene isoprene, gum base, silicone resins and gums, silk and elastin for example, purified from a natural rubbery protein from Ligamentum nuchae.

Another example is carboxypolymethylene which can also be incorporated in the matrix or matrices in order to increase the viscosity of the device and reduce the sorption of saliva thereby also influencing the biodegradation of the device.

According to some embodiments of present invention, the matrix or matrices may be made from any suitable material as described above, such as for example gelatin, in combination with an elasticiser, such as for example soluble elastin, sorbitol or gum base, the gelatin being preferably cross-linked and bound to soluble elastin using any suitable material such as for example glutaraldehyde, nordihydroguaiaretic acid and/or tannic acid. Such matrices have adequate plastic properties and are at the same time of sufficient toughness to maintain the mechanical integrity of the system when affixed at a dental site.

Adhering Agents

Agents may be added to facilitate adhesion to dental surface. Examples are white wax, bees wax, rosin (colophonium bases), shellac, gum mastic and polybutene.

Fillers, Softeners and Binders

The matrix or matrices may also comprise fillers and/or softeners and/or binders such as beeswax, coconut oil, corn syrup, gum Arabic, gum mastic, flour, hydrogenated castor oil, kaolin (aluminum silicate), magnesium oxide, paraffin, silicon dioxide, sodium carboxymethyl-cellulose, xanthan gum, zinc oxide or other various inorganic molecules. It should be noted that certain ions may inhibit remineralization in some cases (for example $P_2O_7$, $HCO_3$, $SiO_4$, $CrO_4$, Mg and Zn) and some inorganic fillers can be coated with water repellant coupling agents such as vinyl silane. Examples of softeners are lecithin and waxes.

Coloring or Staining Agents

These include agents to enhance the appearance of the applied at least one matrix, and dyes which are released to enhance caries detection, as discussed above. Examples are fuchsin or acid red 52 in propylene glycol. These diagnostic dyes include conventional histological stains, clinical decay detection agents and agents whose detection can be enhanced with light, for example fluorescence agents by UV light or other agents activated by intense light within the visual spectrum, or agents drawn by blotting of the lesion after the device or material is removed and the tooth surface rinsed. A color change system could also be used to indicate for example stages of degradation of the device, pH of the site and/or amounts of fluoride at the site. Another application of coloring is the need for marking of the surface to be treated with a dye in the said device which enhances the effects of lasers such as Nd.Yag (Neodymium-Yttrium Aluminum-Garnet lasers, see Miller, M, and Truhe, T. JADA 124:32 (1993)).

Flavoring or Sweetening Agents and Breath Fresheners or Sensates (Warming or Cooling Agents)

A flavoring or sweetening or sensate agent may be added to the matrix or matrices, for example, menthol, sodium saccharin, sorbitol, aspartame, sodium chloride. Also breath fresheners may be added to the matrix or matrices, for example parsley seed, methyl salicylate, sunflower oils and peppermint oil.

It is understood that the invention can include a thickening agent, a sudsing agent, a dessicating agent, an anti-plaque agent, an anti-inflammatory agent, humectants, nutrients, an analgesic or anesthetic agent, antioxidants or another therapeutic or cosmetic agent or mixtures thereof for oral and systemic use/uses.

The matrix or matrices is preferably made from a material, such as for example gelatin cross-linked by glutaraldehyde, nordihydroguaiaretic acid and/or tannic acid that is resorbable and/or biodegradable in the saliva by host enzymes, bacteria or by means of the dissolution properties of the saliva or drinks. Nonetheless, the matrix or matrices may alternatively be made from a non-resorbable material which also releases the active material or materials that is being delivered to the target area. For example, the matrix or matrices may be made from rubber latex, a polymer or any one of a large variety of sugars, lipids, nucleic acids or other proteins found in rubber latex bonded to an amine fluoride which is released in the mouth because of, for example, a host enzyme.

The matrices and devices of this invention and the manufacture thereof are not limited to the above chemical components, but encompass all their variations, and include other chemicals as only examples have been presented above. Further, the biocompatibility of these agents and their interactions need to be carefully examined and tested prior to clinical application.

While some embodiments of the invention have been described by way of illustration, it will be apparent that the invention can be carried into practice with many modifications, variations and adaptations, and with the use of numerous equivalents or alternative solutions that are within the scope of persons skilled in the art, without exceeding the scope of the claims.

The invention claimed is:

1. A method for preventing and/or treating dental disease, in a patient in need thereof, comprising:
    (a) providing a retention device for insertion at a dental site for the controlled delivery to said dental site of at least one material having a predetermined intraoral activity, wherein said device comprises at least one matrix containing said at least one material, said device being in a first configuration, and
        wherein the dental site is an interproximal site or a furcation, said interproximal site comprising an area below the contact area between two dental surfaces or an area of contact of two dental surfaces and surrounding surfaces;
    (b) dampening said retention device with water;
    (c) reshaping said retention device from its said first configuration to a second configuration by bending or folding along an axis thereof which is aligned parallel with the direction of its insertion into said dental site, in which second configuration at least one dimension of said retention device is reduced and said retention device has inner facing and outer facing surfaces; and
    (d) applying said retention device at its said second configuration at said dental site whereby said device is physically affixed and is retained at said dental site in its said second configuration with said outer surfaces resting along said dental surfaces for at least a predetermined time period correlated to the delivery of a predetermined portion of said at least one material to said dental site in a controlled single, bi or multiphase pattern.

2. The method of claim 1, wherein the said first configuration is selected from the group consisting of:
  (a) an H-shape;
  (b) a disc chap;
  (c) a palette shape;
  (d) a C-shape;
  (e) a star shape;
  (f) a Y-shape; and,
  (g) an elongated shape having notches and extensions.

3. The method of claim 2, wherein the notches are shaped to accommodate at least one gingival papilla.

4. The method of claim 2, wherein the extensions are shaped to accommodate col areas.

5. The method of claim 1, wherein said retention device comprises one of the group consisting of the following bending facilitators at the location at which said device is bent:
  (a) an indented bending line;
  (b) a perforated bending line; and,
  (c) an indicating mark along the bending line.

6. The method of claim 5, wherein the indicating mark is a physical line or a chemically treated line.

7. The method of claim 1, wherein the at least one matrix is a polymeric matrix.

8. The method of claim 7, wherein the at least one matrix comprises a hydrophilic polymer that enables said retention device to be affixed by swelling in situ by the hydration of said matrix in the oral cavity after accommodation of said retention device at the dental site.

9. The method of claim 1, wherein the retention device provides at least one agent at a dental site to facilitate changes by chemical or physical means to prevent, seal, eliminate, retard, treat or heal dental disease, cause desensitization, cleanse, induce whitening or bleaching, or breath freshening at a dental surface or restoration surface.

10. The method of claim 1, wherein said retention device is soft for easy interproximal insertion, and provides a cleaning effect which serves as an alternative or supplement to flossing and releases at least one antimicrobial or cleansing agent and/or at least one remineralizing or mineralizing agent.

11. The method of claim 1, wherein said retention device is made from a resilient material enabling the fixing at the dental site.

12. The method of claim 1, wherein said retention device is made from material selected from the group consisting of natural rubber latex (cis 1,4-polyisoprene), PVC (polyvinyl chloride), Nitrile (acrylonitrile and butadiene), Neoprene (chloroprene), plastic (polyethylene) and Tactylon (styrene-based copolymers).

13. The method of claim 1, wherein said retention device is substantially biodegradable.

14. The method of claim 1, wherein said retention device is self-degradable.

15. The method of claim 1, wherein said retention device is substantially resorbable.

16. The method of claim 1, wherein said retention device is substantially non-resorbable.

17. The method of claim 1, wherein said retention device comprises more than one matrix, in a bi-layer, multi-layer, bi-location or multi-location form to deliver said at least one material in a single, bi, or multiphase controlled release pattern for appropriate or optimal delivery time, delivery stage, delivery manor, or delivery form.

18. The method of claim 17, wherein said more than one matrix keeps said at least one material inactive by chemical means or physical separation in order to allow said at least one material to be delivered at an appropriate or optimal time, stage, manner or form.

19. The method of claim 18, wherein said more than one matrix keeps said at least one material separate thereby preventing the premature release or premature interactions of said at least one material.

20. The method of claim 1, wherein said retention device comprises at least one adhesive surface or part thereof that enables said retention device to adhere or be affixed at the dental site.

21. The method of claim 1, wherein said retention device comprises varnishing, coating or encapsulation agent to inhibit unwanted or premature reactions.

22. The method of claim 1, wherein the at least one matrix comprises a synthetic polymer or a natural polymer which may be any one of polysaccharides, lipids, polyisoprene, gum, protein, or any mixture thereof.

23. The method of claim 22, wherein the natural polymer is a protein selected from denatured collagen, gelatin, denatured gelatin, chitosan silk or cellulose.

24. The method of claim 22, wherein the synthetic or natural polymer is cross-linked.

25. The method of claim 22, wherein the synthetic or natural polymer is cross-linked or bound by at least one of glutaraldehyde, formaldehyde, glycol dimethacrylate, tannic acid, allyl methacrylate, nordihydroguaiaretic acid, rosemarinic acid, or is bound by physical means.

26. The method of claim 1, wherein the at least one matrix further comprises any one of an enhancing agent for enhancing the application and release of the said at least one material selected from the group consisting of plasticizers, elasticizers, coloring agents, adhering agents, fillers, softeners, binders, preserving or sterilizing agents, and an auxiliary agent; wherein said auxiliary agent is selected from the group consisting of antimicrobial agents, anti plaque agents, anti inflammatory agents, antioxidants, humoctants, nutrients, analgesic or anaesthetic agents, anti calculus agents, cleaning agents, effervescent agents, tooth desensitizing agents, staining agents, hemostatic agents, whitening or bleaching agents, flavoring or sweetening agents, breath fresheners, and sensates.

27. The method of claim 1, wherein the at least one material is used for the prevention and/or treatment of dental caries.

28. The method of claim 27, wherein said at least one material is a fluoridation agent.

29. The method of claim 27, wherein said at least one material is selected from the group consisting of sodium fluoride, stannous fluoride, stannous hexafluorozirconate, calcium fluoride, difluorosilane, hydrogen fluoride, sodium monofluorophosphate, ytterbium trifluoride, sodium hexafluorosilicate, ammonium fluoride, acidulated phosphate fluoride, an amine fluoride, fluoroaluminosilicate glass and any mixture thereof.

30. The method of claim 27, wherein said at least one material is an amorphous mineral selected from the group consisting of amorphous calcium phosphate, amorphous calcium phosphate fluoride, amorphous calcium carbonate phosphate, amorphous calcium carbonate phosphate fluoride, amorphous calcium fluoride and dicalcium phosphate dehydrate.

31. The method of claim 27, wherein said at least one material is a crystalline mineral selected from the group consisting of aragonite, brushite, calcite, dahltite, ferrhydrite, fluoroapatite, hydroxyapatite, lepidocrocite, magnetite, octacalcium phosphate, vaterite and whitlockite.

32. The method of claim 27, wherein said at least one material is an organic material selected from the group consisting of macromolecules selected from the group consisting of acidic proteins, glycoproteins, sulfated polysaccharides, and smaller molecules that are polyaspartic or polyglutamic acid.

33. The method of claim 1, wherein said at least one material is an enhancing agent or further active agent.

34. The method of claim 1, wherein said at least one material is selected from the group consisting of calcium chloride, calcium bromide, calcium nitrate, calcium acetate, calcium gluconate, calcium benzoate, calcium glycerophosphate, calcium formate, calcium fumarate, calcium lactate, calcium butyrate, calcium isobutyrate, calcium maleate, calcium maleate, calcium propionate, calcium vaerate, alkali salts, ammonium salts of orthophosphoric acid, monopotassium phosphate, dipotassium phosphate tripotassium phosphate, monosodium phosphate, disodium phosphate and trisodium phosphate.

35. The method of claim 1, wherein said at least one material is an acidifying, buffering or pH regulating agent.

36. The method of claim 1, wherein said at least one material is selected from the group consisting of acidulated phosphate fluoride, citric acid, sodium citrate, sodium bicarbonate, calcium carbonate, arginine and polyacrylic acid fully neutralized with alkalimetal ammonium or (alkylol) amine compound sodium polyacrylate.

37. The method of claim 1, wherein said at least one material is an antimicrobial agent.

38. The method of claim 1, wherein said at least one material is selected from the group consisting of stannous fluoride, alexidine, chlorhexidine digluconate, hexetidine, copper zinc citrate and stannous pyrophosphate, triclosan, cetylpyridinium chloride and halogenated bisphenolic compounds.

39. The method of claim 1, wherein said at least one material serves as a cleaning agent.

40. The method of claim 1, wherein said at least one material is selected from the group consisting of sodium alkyl sulfate, sodium lauryl sulfate, sodium coconut monoglyceride sulfonates, sodium lauryl sarcosinate, taurates, sodium lauryl sulfoacetate, sodium lauroyl isothionate, sodium laureth carboxylate, sodium dodecyl benzenesulfonate, poloxamers, polyoxyethylene sorbitan esters, fatty alcohol ethoxylates, polyethylene oxide, cocamidoppropyl betaine, sodium bicarbonate, monosodiumphosphate, sodium hydroxide, potassium hydroxide, sodium carbonate and imidazole.

41. The method of claim 1, wherein said at least one material serves as an effervescing agent.

42. The method of claim 1, wherein said at least one material is a sodium bicarbonate and citric acid system.

43. The method of claim 1, wherein said at least one material serves as a tooth desensitizing agent.

44. The method of claim 1, wherein said at least one material is selected from the group consisting of fluorides, potassium citrate, potassium chloride, potassium tartrate, potassium bicarbonate, potassium oxalate and potassium nitrate.

45. The method of claim 1, wherein said at least one material is a tooth whitening agent.

46. The method of claim 45, wherein said tooth whitening agent is selected from the group consisting of hydrogen peroxide, carbamide peroxide metal chlorites, perborates, percarbonates, peroxyacids, persulfates, urea peroxide, calcium peroxide, calcium chlorite, barium chlorite, magnesium chlorite, lithium chlorite, sodium chlorite, potassium chlorite, hypochlorite, chlorine dioxide, sodium percarbonate, oxones, and protease.

47. The method of claim 1, for cleaning a dental site in a patient in need thereof, wherein said at least one material is at least one cleaning material.

48. The method of claim 1, for desensitizing a dental site in a patient in need thereof, wherein said at least one material is at least one desensitizing material.

49. The method of claim 1, for whitening a dental site in a patient in need thereof, wherein said at least one material is at least one whitening material.

50. The method of claim 1, for freshening breath in a patient in need thereof, wherein said at least one material is at least one breath freshening material.

51. The method of claim 9, wherein said chemical or physical means are electrodes or laser, respectively.

* * * * *